United States Patent
Motai

(10) Patent No.: US 10,765,448 B2
(45) Date of Patent: Sep. 8, 2020

(54) MEDICAL INSTRUMENT INTRODUCTION DEVICE AND TREATMENT METHOD OF USING THE SAME

(71) Applicant: OLYMPUS CORPORATION, Hachioji-shi, Tokyo (JP)

(72) Inventor: Kosuke Motai, Hidaka (JP)

(73) Assignee: OLYMPUS CORPORATION, Tokyo (JP)

(*) Notice: Subject to any disclaimer, the term of this patent is extended or adjusted under 35 U.S.C. 154(b) by 297 days.

(21) Appl. No.: 15/844,784

(22) Filed: Dec. 18, 2017

(65) Prior Publication Data

US 2018/0103980 A1   Apr. 19, 2018

Related U.S. Application Data

(63) Continuation of application No. PCT/JP2016/065890, filed on May 30, 2016.

(30) Foreign Application Priority Data

Jul. 9, 2015   (JP) .................................. 2015-137597

(51) Int. Cl.
  *A61B 17/34*   (2006.01)
  *A61B 1/00*   (2006.01)

(52) U.S. Cl.
  CPC .......... *A61B 17/3417* (2013.01); *A61B 17/34* (2013.01); *A61B 17/3415* (2013.01);
  (Continued)

(58) Field of Classification Search
  CPC .............. A61B 17/341; A61B 17/3415; A61B 17/3417; A61B 1/00082; A61B 2018/00285
  See application file for complete search history.

(56) References Cited

U.S. PATENT DOCUMENTS

| 5,383,889 A  * | 1/1995 | Warner ............ A61B 17/00234 604/908 |
| 2005/0165432 A1* | 7/2005 | Heinrich ............ A61B 17/3417 606/167 |

(Continued)

FOREIGN PATENT DOCUMENTS

| JP | S56-166006 U | 12/1981 |
| JP | 2000-198093 A | 7/2000 |

(Continued)

OTHER PUBLICATIONS

Jan. 8, 2019 Extended Search Report issued in European Patent Application No. 16821117.5.

(Continued)

*Primary Examiner* — Michael F Peffley
*Assistant Examiner* — Bo Ouyang
(74) *Attorney, Agent, or Firm* — Oliff PLC

(57) ABSTRACT

A medical instrument introduction device, includes an outer tube portion indwelled within a body wall; and an inner needle portion inserted through the outer tube portion, wherein the outer tube portion includes a base portion; a tubular conduit portion whose proximal end portion is connected to the base portion; and an anchor portion connected to a distal end portion of the conduit portion, wherein the conduit portion has a bellows folded shape in a natural state, a dimension of the conduit portion in an axial direction being capable of being increased as the folded shape is stretched by the inserted inner needle portion, and a force needed for stretching the folded shape being gradually decreased in a direction from the proximal end portion to a distal end portion of the conduit portion, and the anchor portion and the inner needle potion are couplable with each other.

7 Claims, 8 Drawing Sheets

(52) U.S. Cl.
CPC ............ *A61B 1/00* (2013.01); *A61B 1/00064* (2013.01); *A61B 1/00131* (2013.01); *A61B 2017/3443* (2013.01); *A61B 2017/3454* (2013.01)

(56) References Cited

U.S. PATENT DOCUMENTS

| | | | |
|---|---|---|---|
| 2009/0287240 A1* | 11/2009 | Yamatani | A61B 17/3421 606/192 |
| 2011/0144440 A1 | 6/2011 | Cropper et al. | |
| 2013/0053779 A1* | 2/2013 | Shelton, IV | A61B 17/3421 604/164.04 |

FOREIGN PATENT DOCUMENTS

| | | |
|---|---|---|
| JP | 2012-045398 A | 3/2012 |
| JP | 5498056 B2 | 5/2014 |
| JP | 2014-239907 A | 12/2014 |
| WO | 2008/015566 A2 | 2/2008 |
| WO | 2010/042913 A2 | 4/2010 |

OTHER PUBLICATIONS

Aug. 9, 2016 International Search Report issued in International Patent Application No. PCT/JP2016/065890.

Aug. 8, 2017 Notice of Allowance issued in Japanese Patent Application No. 2017-511811.

* cited by examiner

MEDICAL INSTRUMENT INTRODUCTION DEVICE AND TREATMENT METHOD OF USING THE SAME

BACKGROUND OF THE INVENTION

Field of the Invention

The present invention relates to a medical instrument introduction device and a treatment method of using the medical instrument introduction device.

This application is a continuation application based on a PCT International Application No. PCT/JP2016/065890, filed on May 30, 2016, whose priority is claimed on Japanese Patent Application No. 2015-137597, filed on Jul. 9, 2015. The contents of both of the PCT International Application and the Japanese Patent Application are incorporated herein by reference.

Description of Related Art

Conventionally, Endoscopic Submucosal Dissection (ESD) performed by an endoscope inserted into the gastrointestinal tract and the like is known. Comparing to other surgical procedures such as Endoscopic Mucosal Resection (EMR) and the like, tissue distributed in a wider area is dissected by performing the ESD. Regarding internal organs having a comparatively narrow cavity such as the esophagus, the duodenum, the large intestine, and the like, a direction for approaching a target site is limited such that it becomes difficult to perform the ESD.

In order to lower the difficulty of performing the ESD in the internal organs having a narrow cavity, it is considered to furtherly introduce medical instruments that have been introduced into the abdominal cavity into such internal organs, then perform the surgical procedures by collaborating the medical instruments with an endoscope inserted into the gastrointestinal tract and a treatment device for an endoscope. In Japanese Patent No. 5498056, a related medical instrument introduction device is disclosed that the medical instrument introduction device can introduce a medical instrument into the thoracic cavity or the urinary bladder by inserting the medical instrument introduction device through the abdominal wall.

SUMMARY OF THE INVENTION

According to a first aspect of the present invention, a medical instrument introduction device includes an outer tube portion that is indwelled within a body wall and an inner needle portion that is inserted through the outer tube portion, wherein the outer tube portion includes a base portion disposed at a proximal side of the outer tube portion, a tubular conduit portion, the conduit portion being formed of a stretchable material, a proximal end portion of the conduit portion being connected to the base portion, and an anchor portion connected to a distal end portion of the conduit portion, wherein the conduit portion has a bellows folded shape in a natural state, wherein a dimension of the conduit portion in an axial direction is capable of being increased as the folded shape is stretched by the inserted inner needle portion, and wherein a force needed for stretching the folded shape is gradually decreased in a direction from the proximal end portion to the distal end portion of the conduit portion, and wherein the anchor portion and the inner needle potion are couplable with each other such that the anchor portion moves following an advancement or a retraction of the inner needle portion.

According to a second aspect of the present invention, in the medical instrument introduction device according to the first aspect, the anchor portion may be deformable such that a maximum dimension of the anchor portion in a radial direction is larger than a dimension of the conduit portion in the radial direction.

According to a third aspect of the present invention, in the medical instrument introduction device according to the second aspect, the anchor portion may include a balloon which is expandable and shrinkable.

According to a fourth aspect of the present invention, in the medical instrument introduction device according to any of the first to third aspect, the inner needle portion may include a cauterization portion arranged at a distal end of the inner needle portion, the cauterization portion being configured to cauterize tissue by conducting electric current to the cauterization portion.

According to a fifth aspect of the present invention, a treatment method on a target site in a luminal organ inside a body cavity by using the medical instrument introduction device according to claim 1 and a flexible endoscope, the treatment method includes a step of determining an indwelling position at which the outer tube portion of the medical instrument introduction device is to be indwelled within a body wall of the body cavity; a step of forming a first opening communicating with the body cavity at the indwelling position; a step of inserting the outer tube portion into the body cavity from a side of the anchor portion through the first opening, an insertion amount of the outer tube portion being determined such that at least the base portion is positioned outside the body cavity; a step of inserting the endoscope through a natural opening and indicating an opening formation position at which a second opening communicating with the luminal organ inside the body cavity being formed, by using the endoscope, in order to confirm the opening formation position from outside of the luminal organ; a step of inserting the inner needle portion into the outer tube portion until a distal end portion of the inner needle portion protrudes from the anchor portion and reaches a vicinity of the opening formation position, a bellows folded shape of the conduit portion being stretched; a step of forming the second opening at the opening formation position by using the inner needle portion; and a step of inserting the anchor portion into the luminal organ through the second opening, and deforming the anchor portion such that a dimension of the anchor portion in a radial direction becomes larger than that of the conduit portion to engage the anchor portion with the luminal organ.

According to a sixth aspect of the present invention, the treatment method according to the fifth aspect may further include a step of removing the inner needle portion via the outer tube portion after the anchor portion is engaged with the wall of the luminal organ, a step of inserting a medical instrument through the outer tube portion into the inside of the luminal organ, a step of performing a treatment on the target site using the medical instrument together with another medical instrument introduced by the endoscope, a step of removing the medical instrument through the outer tube portion after the treatment on the target site is finished, and a step of shrinking the anchor portion and removing the outer tube portion from the luminal organ and the body cavity.

DETAILED DESCRIPTION OF THE INVENTION

A first embodiment of the present invention will be described by referring FIGS. 1 to 8. A medical instrument introduction device according to the present embodiment has an outer tube portion that is inserted through a body wall such as the abdominal wall and the thoracic wall, and an inner needle portion that is inserted into the outer tube portion.

Figure 1:
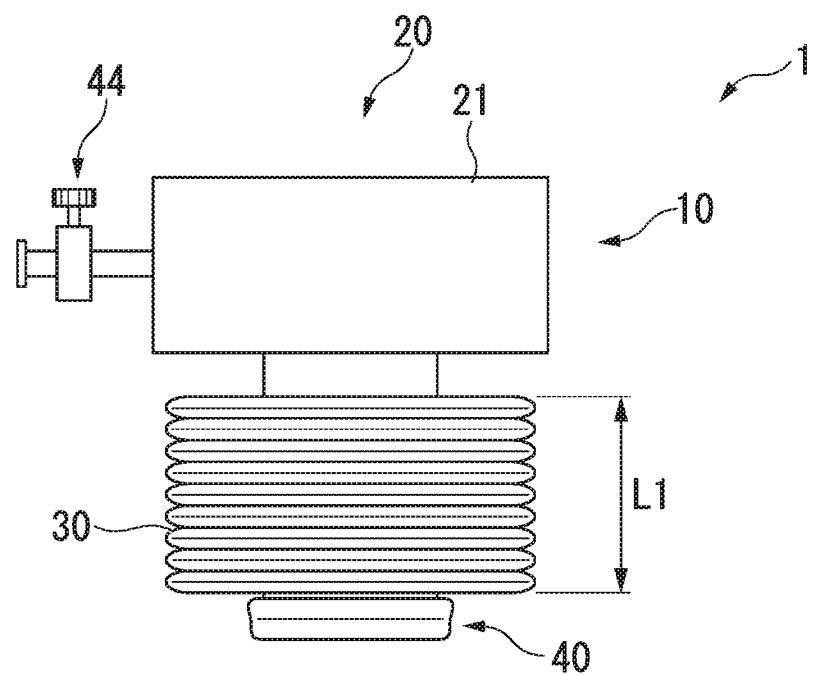
FIG. 1 is a view showing an outer tube portion of a medical instrument introduction device according to a first embodiment of the present invention.

FIG. 1 is a view showing an outer tube portion 10 of a medical instrument introduction device 1. The outer tube portion 10 has a base portion 20 that is disposed outside the body cavity, a conduit portion that is connected to the base portion 20, and an anchor portion 40 that is connected to a distal portion of the conduit portion 30.

Figure 2:
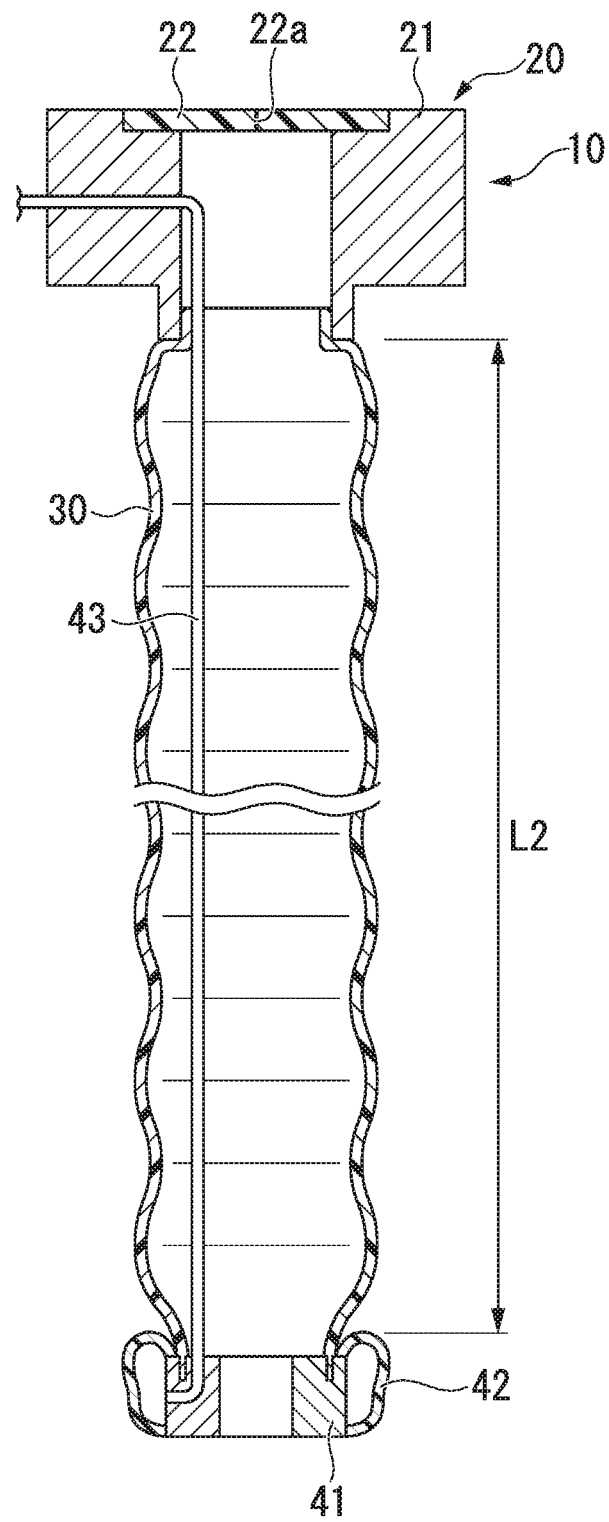
FIG. 2 is a cross-sectional view showing a stretched state of the outer tube portion.

FIG. 2 is a cross-sectional view showing a stretched state of the outer tube portion 10. The base portion 20 has a tubular base member 21. A proximal end portion of the conduit portion 30 is connected to a distal end side of the base member 21 for ensuring airtightness by using a method such as adhesive and the like. An opening opened at a proximal side of the base member 21 is airtightly closed by a valve member 22 formed of a material such as rubber and the like. The valve member 22 has a slit 22a. An inner needle portion that will be described later can be inserted into the outer tube portion 10 while retaining the airtightness, by inserting the inner needle portion through the slit 22a.

The conduit portion 30 is formed of a flexible material such as rubber that is elastically deformable and the like, and the conduit portion 30 is formed in a tubular shape that is expandable and foldable. As shown in the FIG. 1, when the conduit portion 30 is in a natural state in which an external force is not applied to the conduit portion 30, the conduit portion 30 is folded to be a bellows such that a dimension of the conduit portion 30 in an axial direction becomes shorter. When a force is applied to the distal end portion of the conduit portion 30 in the natural state, wherein the force is applied in a direction to separate the distal end portion of the conduit portion 30 from the proximal end portion, as shown in FIG. 2, the bellows folded shape is stretched. As a result, the dimension of the conduit portion 30 in the axial direction becomes longer, while a dimension of the conduit portion in a radial direction becomes shorter.

Regarding the conduit portion 30, it can properly set the dimension in the axial direction L1 (see FIG. 1) in the natural state and the dimension in the axial direction L2 (see FIG. 2) in the state in which the bellows folded part is completely stretched. For example, the dimension L1 may be set to be equal to 100 millimeters (mm) or shorter than 100 millimeters, and the dimension L2 may be set to be in a range from 150 millimeters to 500 millimeters. It is preferable to set the dimension L2 longer since more types of lesions can be treated. The dimension in the radial direction of the conduit portion 30 in the natural state tends to increase, if the dimension L2 becomes longer and the dimension L1 becomes shorter. When the dimension in the radial direction of the conduit portion 30 in the natural state becomes longer, since an incision size to the body wall necessary for using the medical instrument introduction device becomes larger, it is preferable to set the dimensions L1 and L2 in consideration of balance between the two dimensions.

Figure 3:
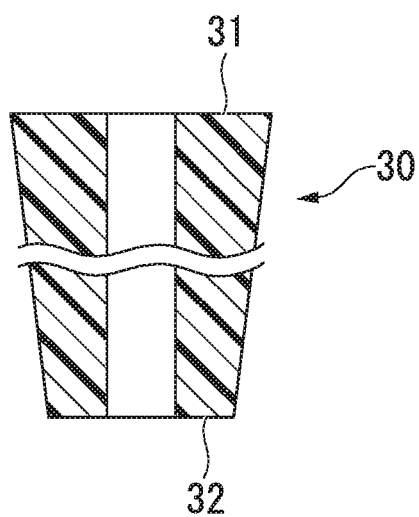
FIG. 3 is a schematic view showing a conduit portion of the outer tube portion.

FIG. 3 is a schematic view showing a configuration of the conduit portion 30. In the conduit portion 30, a proximal end portion 31 connected with the base portion 20 is thickest. The conduit portion 30 is formed to be gradually thinner in a direction from the proximal end portion 31 toward a distal end portion 32 to which the anchor portion 40 is attached. According to such a configuration, the force applied to the distal end portion 32 which is necessary to stretch the bellows folded shape of the conduit portion 30 is smallest, and the force applied to the proximal end portion 31 which is necessary to stretch the bellows folded shape of the conduit portion 30 is biggest. Accordingly, when the conduit portion 30 starts to be stretched from the natural state, firstly the distal end portion 32 starts to be stretched, and when the conduit portion 30 starts to return to the natural state, firstly the proximal end portion 31 returns.

The force necessary to stretch the folded shape may continuously decrease in a direction from the proximal end side to the distal end side of the conduit portion 30, and the force necessary to stretch the folded shape may discontinuously decrease in a step-wise manner in the direction from the proximal end side to the distal end side of the conduit portion 30.

Accordingly, the variation of the thickness of the conduit portion 30 is not limited to an aspect that the thickness of the conduit portion 30 continuously becomes thinner as shown in FIG. 3, the conduit portion 30 may become thinner in a step-wise manner. In such a situation, the conduit portion may be configured by arranging tubular members with different thicknesses in the axial direction and airtightly connecting the tubular members.

Shown as FIG. 1 and FIG. 2, the anchor portion 40 has a circular distal end member 41 connected to the conduit portion 30 and a balloon 42 attached to an outer circumference surface of the distal end member 41.

The distal end member 41 is formed of a material such as metal or resin and the like. An outer diameter of the distal end member 41 is substantially the same with an inner diameter of the conduit portion 30 in a state in which the conduit portion 30 is stretched to the dimension L2.

The balloon 42 only needs to be expandable by supplying fluids to the inside therewith. The balloon 42 may be formed of either a material with superior expandability or a material with inferior expandability. The balloon 42 is connected to a tube 43 provided for supplying the fluids. The tube 43 is attached to the distal end member 41 in a manner of passing through a lateral wall of the distal end member 41. The tube 43 extends through inside of the conduit portion 30 and reaches inside of the base portion 20. The tube 43 further passes through a lateral wall of the base member 21 of the base portion 20 to extend to an outside of the outer tube portion 10, and the tube 43 can be connected to a fluid supply source (not shown). Since the tube 43 is not fixed with respect to the base member 21, a length of the tube 43 disposed inside the conduit portion 30 can be adjusted by pulling part of the tube 43 outside of the outer tube portion 10 in accordance with a length of the conduit portion 30. The balloon 42 can be kept to an expanded state by closing a valve 44 provided at the tube (see FIG. 1).

Figure 4:
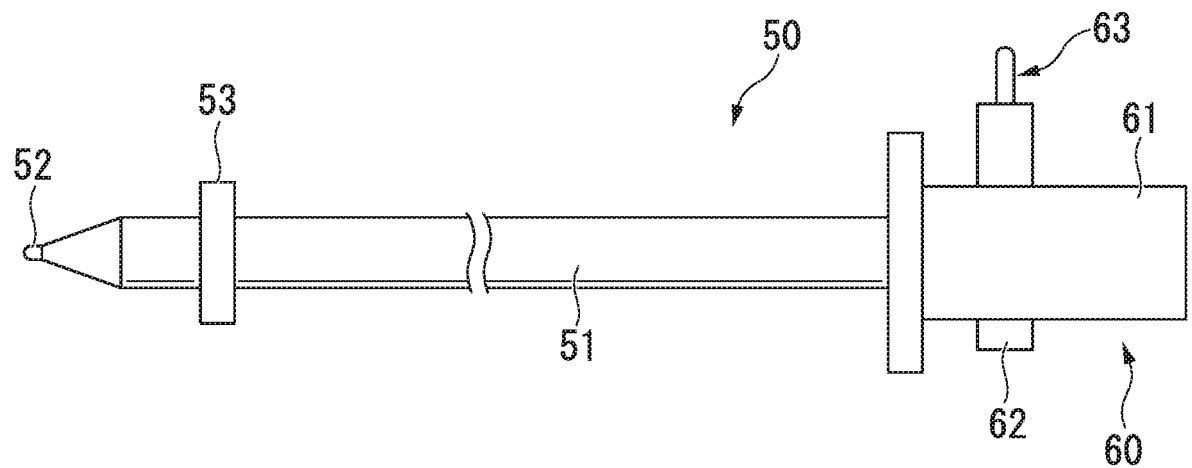
FIG. 4 is a view showing an inner needle portion of the medical instrument introduction device.

FIG. 4 is a view showing an inner needle portion 50 of the medical instrument introduction device. The inner needle portion 50 has an elongated and rigid main body 5l, a cauterization portion 52 provided at a distal end of the main body 51, and an operation portion 60 provided at a proximal end portion of the main body 51.

The main body 51 is formed of a material of metal and the like, and the main body 51 is formed in a substantially cylindrical shape. A distal end side of the main body 51 is formed in a tapered shape such that the diameter of the main body becomes smaller toward the distal end side thereof. A disk-shaped flange 53 is attached to the main body. The dimension in a radial direction of the flange 53 is set to be smaller than an inner diameter of a hole of the base portion 20 and an inner diameter of the conduit portion 30, while larger than an inner diameter of the distal end member 41. Accordingly, the inner needle portion 50 can be inserted into the outer tube portion 10 until the flange 53 abuts against the proximal end of the distal end member 41. In the state in which the flange 53 abuts against the distal end member 41, the taper-shaped part of the main body 51 of the inner needle portion 50 projects from the outer tube portion 10.

The cauterization portion 52 projects from a distal end of the main body 51. The cauterization portion 52 is formed of an electric conductor material. It is possible to use the cauterization portion 52 to perform cauterization and incision to tissue by conducting electric currently to the cauterization portion 52. Regarding the cauterization portion 52, specific mechanism of the cauterization portion 52 for performing the cauterization and incision to tissue is not limited, for example, well-known mechanisms such as a high-frequency knife or a heat probe and the like can be appropriately chosen. The cauterization portion 52 is connected to wirings for conducting the electric current (not shown). The wirings pass through the main body 51 and extend to the operation portion 60.

The operation portion 60 has a grip 61 grasped by a user, and a switch 62 and a plug 63 provided at the grip 61. The plug 63 is connected to the wirings (not shown) that are connected to the cauterization portion 52. Electric currently can be conduct to the cauterization portion 52 via the wirings by connecting the plug 63 to a power source. Switching On/Off of the electric currently to the cauterization portion 52 can be performed by operating the switch 62.

Operations of using the medical instrument introduction device 1 according to the present embodiment having the above-described outer tube portion 10 and the inner needle portion 50 will be described herewith by taking a situation in which the target site of the treatment is in the large intestine (luminal organ) as an example.

Firstly, the user determines an indwelling position at which the outer tube portion 10 of the medical instrument introduction device 1 is to be indwelled within the abdominal wall while taking a position of the target site of the treatment into consideration. Then, the user performs forms a small incision at the indwelling position on part of the abdominal wall, and the user forms an incision (first opening) continuing to an internal of the abdominal cavity at the indwelling position. The size of the small incision is set such that the conduit portion 30 in the natural state can comfortably be inserted into the incision.

Subsequently, the user inserts the outer tube portion 10 into the incision on the abdominal wall from a side of the anchor portion 40.

At this time, an insertion amount of the outer tube portion 10 is set such that at least the base portion 20 is positioned outside the body. Meanwhile, the user indwells a trocar used for inserting observation means such as a laparoscope and the like at another position on the abdominal wall, and then inserts the trocar to establish an observation environment for observing the medical instrument introduction device 1 inside the body cavity.

The user indicates an opening formation position for accessing the target site by using an aspect of inserting a flexible endoscope from a natural opening such as the anus and the like for capturing the target site from inside of the large intestine and confirming the target site from outside of the large intestine in the body cavity. A method of indicating the opening formation position is not specifically limited, and a well-known method can be appropriately selected and used. For example, methods such as pressing the opening formation position by an endoscope or a treatment device inserted in the endoscope to cause the opening formation position to swell, spotting at the opening formation position, illuminating the opening formation position from outside of the hollow organ to cause the opening formation position to be capable of visually confirmed, and the like can be considered. The operation of indicating the opening formation position may be performed by another person different with the user.

The user confirms positions of the outer tube portion 10 and the opening formation position by using the observation means, while inserting a distal end of the inner needle portion 50 into the inside of the outer tube portion 10 through the slit 22a of the valve member 22. After the flange 53 of the inner needle portion 50 comes into contact with a proximal end side of the distal end member 41 and when the user further inserts the inner needle portion 50 into the outer tube portion 10, the anchor portion 40 moves to be separated from the base portion 20 the bellows folded shape of the conduit portion 30 is stretched from the distal end side thereof. The user makes the dimension of the conduit portion 30 in the axial direction to be increased by inserting the inner needle portion 50, while moving the distal end portion of the inner needle portion 50 protruded from the anchor portion 40 to the vicinity of the opening formation position.

Figure 5:
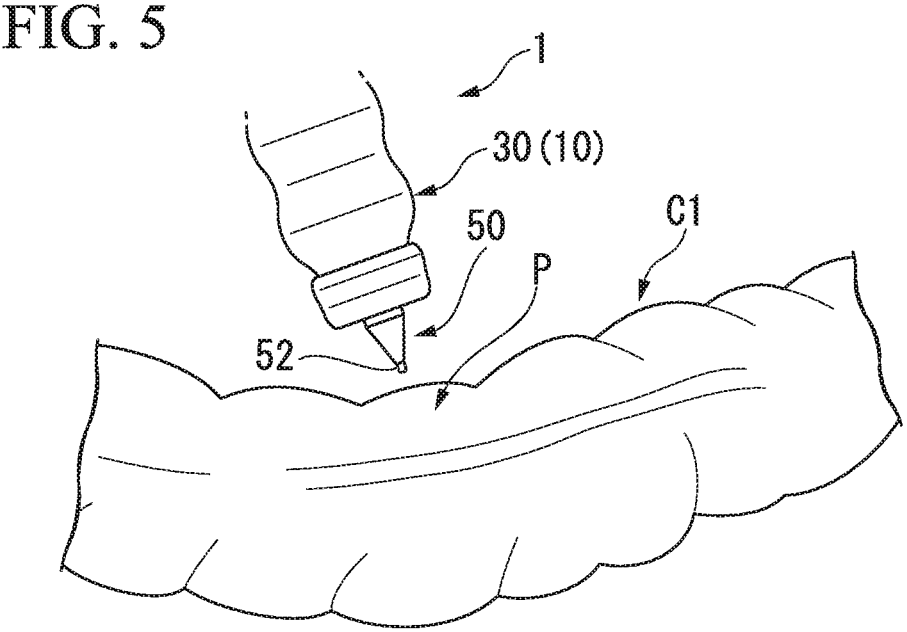
FIG. 5 is a view showing an action of the medical instrument introduction device while being used.

As shown in FIG. 5, when the distal end portion of the inner needle portion 50 reaches the vicinity of the opening formation position, the user makes the energized cauterization portion 52 to be in contact with the opening formation position P of the large intestine C1 for forming an opening (second opening) in communication with the inside of the large intestine C1 at the opening formation position P. When the second opening is formed, the user turns off the cauterization portion 52 and then inserts a distal end portion of the medical instrument introduction device 1 into the large intestine C1 through the opening.

When the opening is not suitably formed by the cauterization portion 52, the second opening may be formed by puncturing the distal end portion of the inner needle portion 50 into the wall of the large intestine and penetrating the wall of the large intestine. In such a situation, assistance operations for making the puncture operation easier, such as supporting the puncture position by the endoscope and the treatment instrument protruded from the endoscope that are inserted into the large intestine, and strengthening the air supply into the digestive tract for applying a tension on the opening formation position, may be performed. Such assistance operations may be performed during the formation of the second opening using the cauterization portion 52.

Figure 6:
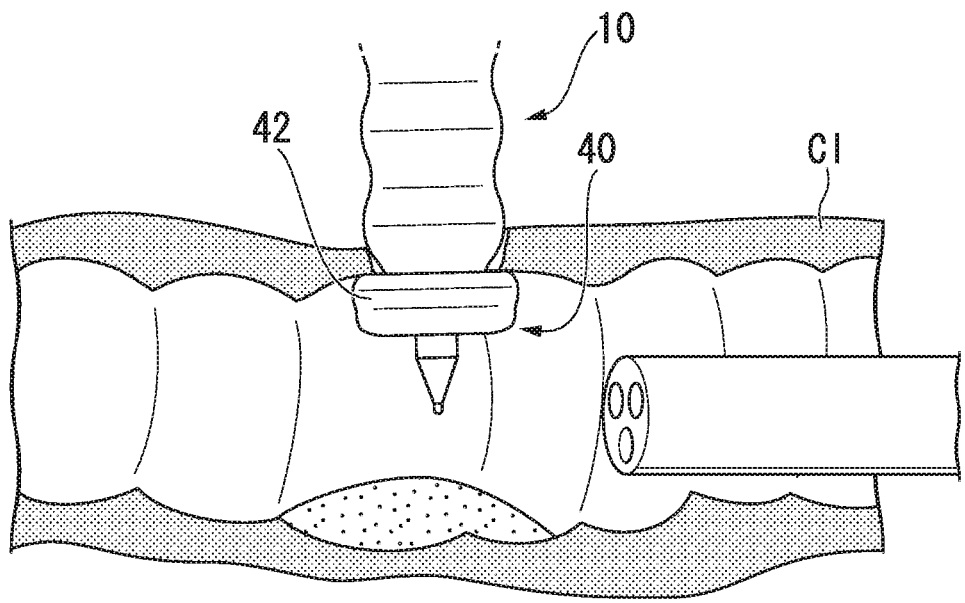
FIG. 6 is a view showing an action of the medical instrument introduction device while being used.

When the anchor portion 40 is moved into the large intestine, the user opens the valve 44 to introduce the fluids into the balloon 42 through the tube 43. As shown in FIG. 6, the balloon 42 is expanded by the fluids introduced into the balloon 42. The anchor portion 40 is deformed such that the dimension of the anchor portion 40 in the radial direction becomes larger than the dimension of the conduit portion due to the expansion of the balloon 42. As a result, the anchor portion 40 is engaged with the wall of the large intestine C1 such that the anchor portion 40 cannot be removed from the opening on the wall of the large intestine. Thus, the medical instrument introduction device 1 is indwelled within the large intestine C1 and cannot be removed from the large intestine C1. In a state in which the medical instrument introduction device 1 is indwelled within the large intestine C1, a route formed by the outer tube portion 10 is established such that it is possible to directly access the inside of the large intestine C1 from outside of the abdominal wall.

Figure 7:
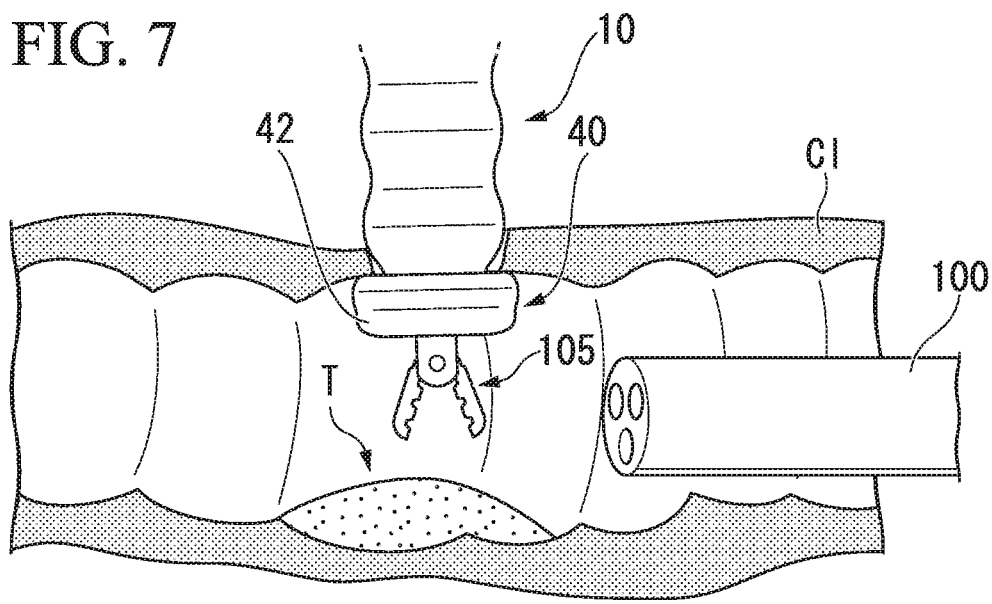
FIG. 7 is a view showing an action of the medical instrument introduction device while being used.

After the medical instrument introduction device 1 is indwelled within the large intestine C1, the user removes the inner needle portion 50 from the outer tube portion 10, and as shown in FIG. 7, the user inserts the medical instrument used for performing treatment to the target site T from the base portion (see FIG. 2) into the outer tube portion 10 for introducing the medical instrument into the large intestine C1. In FIG. 7, a grasping forceps 105 is shown as an example of the medical instrument.

Figure 8:
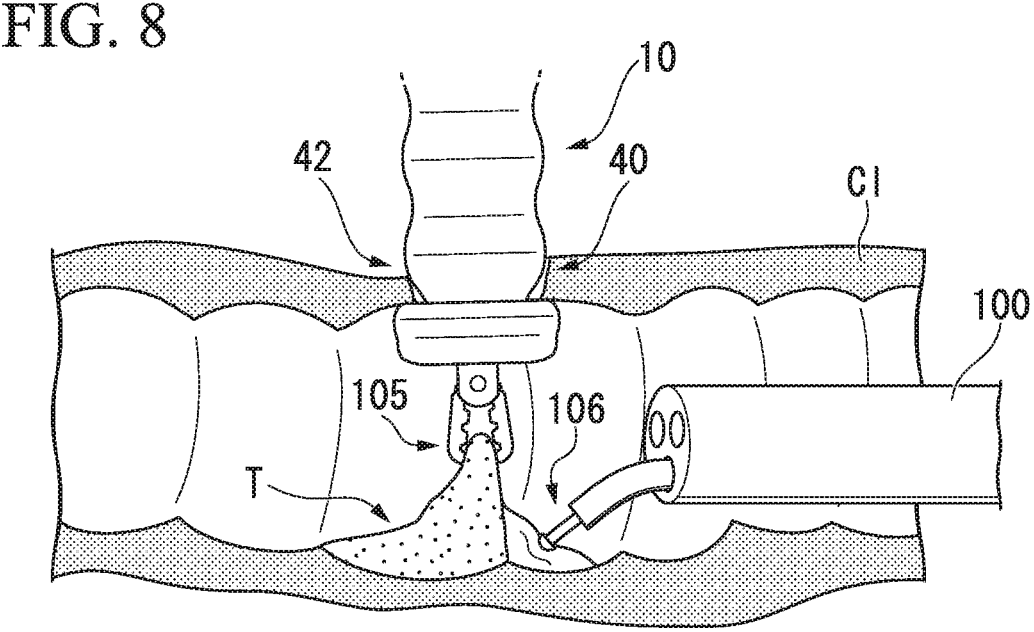
FIG. 8 is a view showing an action of the medical instrument introduction device while being used.

Subsequently, the user performs treatment to the target site T by using the flexible endoscope 100 and the medical instrument introduced by the medical instrument introduction device 1. For example, as shown in FIG. 8, the user pulls the target site T by using the grasping forceps 105 so as to apply a tension to the target site T for forming a treatment space, and performs an incision treatment to the target site T by using the treatment devices such as an high-frequency knife 106 that protrudes from a channel of the flexible endoscope 100. To the contrary, the user may form the treatment space by using the grasping forceps that protrudes from the flexible endoscope 100, and perform the incision treatment to the target site by using the high-frequency knife introduces through the outer tube portion 10. In a situation that part of the tissue is removed during the treatment, the tissue can be collected without contacting other organs in the abdominal cavity by grasping the pulling the medical instrument outside the body cavity through the outer tube portion 10. Also, the removed tissue may be collected by using the flexible endoscope 100 with the same procedures of ordinary ESD treatment.

The medical instrument introduced by the medical instrument introduction device 1 can approach the target site T from a different direction with respect to a direction from which the treatment device introduced by the flexible endoscope 100 approaches the target site T. Accordingly, even in the hollow organs with a narrow inner cavity such at the large intestine and the like, the difficulty of ESD treatment and the like can be significantly reduced by performing the treatment due to a collaboration of the treatment instruments.

The medical instrument introduced by the medical instrument introduction device 1 only has to have a dimension so as to be capable of inserting through the outer tube portion 10, and the medical instrument is not specifically limited. Accordingly, the medical instrument introduced by the medical instrument introduction device 1 may be a flexible treatment device, or a rigid treatment device without flexibility. As disclosed in Japanese Unexamined Patent Application, First Publication No. 2008-132352, a medical instrument having an observation mechanism and a plurality of arms can be introduced into the body using the medical instrument introduction device 1 according to the present embodiment. In the situation that the medical instrument introduced by the medical instrument introduction device 1 has the observation mechanism, the target site T can be observed from different angles and the treatment procedure can be more suitably performed.

After the treatment to the target site is finished, the user withdraws the fluids from the balloon 42 to shrink the balloon the balloon 42, and the user removes the outer tube portion 10 from the large intestine. Further, the user extracts the outer tube portion 10 to remove the outer tube portion 10 from the abdominal wall. The removal of the outer tube portion 10 may be performed after the removal of the inserted medical instrument, and may be performed while the inserted medical instrument is still inserted through the outer tube portion 10.

Figure 9:
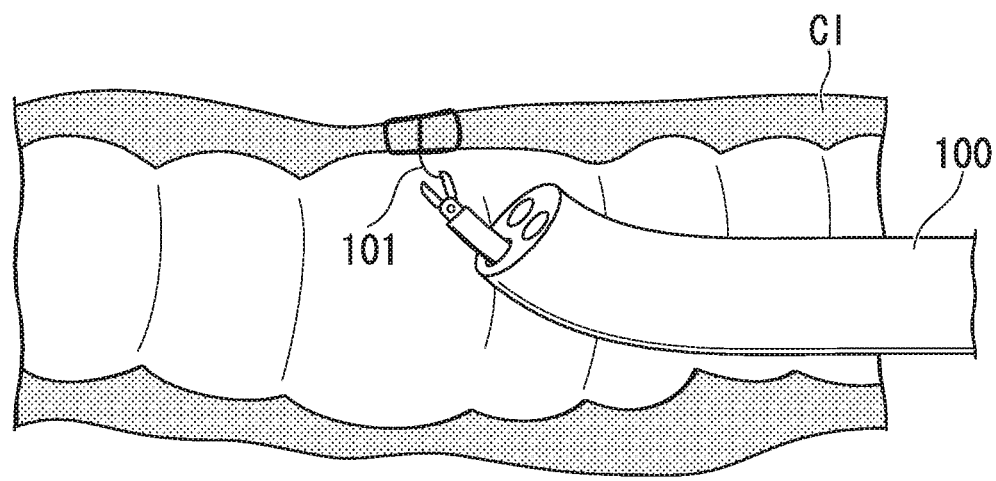
FIG. 9 is a view showing an action of closing an opening after the treatment.

The user sutures the incision formed at the large intestine using a known suture device. The suture may be performed on a side of the abdominal wall, and the suture treatment may be performed inside the large intestine C1, as shown in FIG. 9. Methods of the suture are not specifically limited that either of the methods, such as a method of using a suture thread 101, a method of using a suture unit having an anchor a suture thread, and a method of using clips, staples, and the like, is applicable.

As the above-mentioned description, according to the medical instrument introduction device 1 according to the present embodiment, since the outer tube portion 10 is configured that the dimension of the conduit portion 30 in the axial direction is changeable, the length of the outer tube portion 10 is changeable in accordance with the distance between the indwelling position and the opening formation position such that a variety of patterns can be suitably handled. As a result, the medical instrument can be suitably introduced into the luminal organs through the abdominal wall.

Since the conduit portion 30 is configured to have a bellows folded shape, a difference between a dimension in the axial direction of the conduit portion 30 in an initial state and a dimension in the axial direction of the conduit portion 30 in a longest state can be set to be large, wherein the dimension in the axial direction of the conduit portion 30 in the initial state is a minimum value, and the dimension in the axial direction of the conduit portion 30 in the longest state is a maximum value. As a result, a large range of the distance between the indwelling position and the opening formation position, with which the outer tube portion 10 is applicable, can be secured. Furthermore, since the dimension in the axial direction of the conduit portion 30 in the longest state can be set to be enough long, even in a situation in which the indwelling position and the opening formation position is greatly separated, a strong tension due to the restoration of the conduit portion 30 when the stretched conduit portion 30 is to restore to the original length is difficult to be generated, and thus sufferings to the luminal organs with which the conduit portion 30 is indwelled can be suppressed.

The conduit portion 30 has a configuration that the distal end side thereof is easier to be stretched and compressed than the proximal end side thereof such that the bellows folded shape of the distal end side of the conduit portion 30 is difficult to be remained when the conduit portion 30 is stretched. Accordingly, it is possible to lower the possibility that the distal end of the inner needle portion 50 is obscured by the bellows folded shape and becomes difficult to be visually confirmed during the opening formation at the opening formation position. As a result, the user can reliably forms the opening while suitably observing the distal end portion of the inner needle portion 50 such as the cauterization portion 52 by using a laparoscope or the like.

Since the anchor portion 40 has the balloon 42, the user can suitably retain a state of engaging the medical instrument introduction device 1 with the luminal organs during the treatment, and the user can shrink the balloon 42 for decreasing the resistance during the insertion and the removal of the medical instrument introduction device 1.

Since the inner needle portion 50 has the cauterization portion 52 at the distal end thereof, a great force is not required at the time of forming the opening at the luminal organs. Accordingly, even in a situation in which the treatment target is the luminal organ with a thin wall, it is possible to suitably avoid any excessive incision during the opening formation and the like.

However, in the medical instrument introduction device according to the present invention, the cauterization unit is a preferable configuration but not an essential configuration. Accordingly, an inner needle portion having a blade and the like that can dissect the tissue and is disposed at the distal end portion of the inner needle portion is also applicable to suitably introduce the medical instrument into the luminal organs through the abdominal wall.

Next, a second embodiment of the present invention will be described by referring to FIGS. 10 to 12. The difference between the medical instrument introduction device according to the present embodiment and the medical instrument introduction device 1 according to the first embodiment is the engagement configuration of the outer tube portion and the inner needle portion. In the following description, the same reference numerals will be given to configurations which are common to those which are previously described, and thus, a repeated description will be omitted.

The medical instrument introduction device 70 according to the present embodiment has an outer tube portion 71 and an inner needle portion 80 instead of the outer tube portion 10 and the inner needle portion 50 disclosed in the first embodiment.

Figure 10:
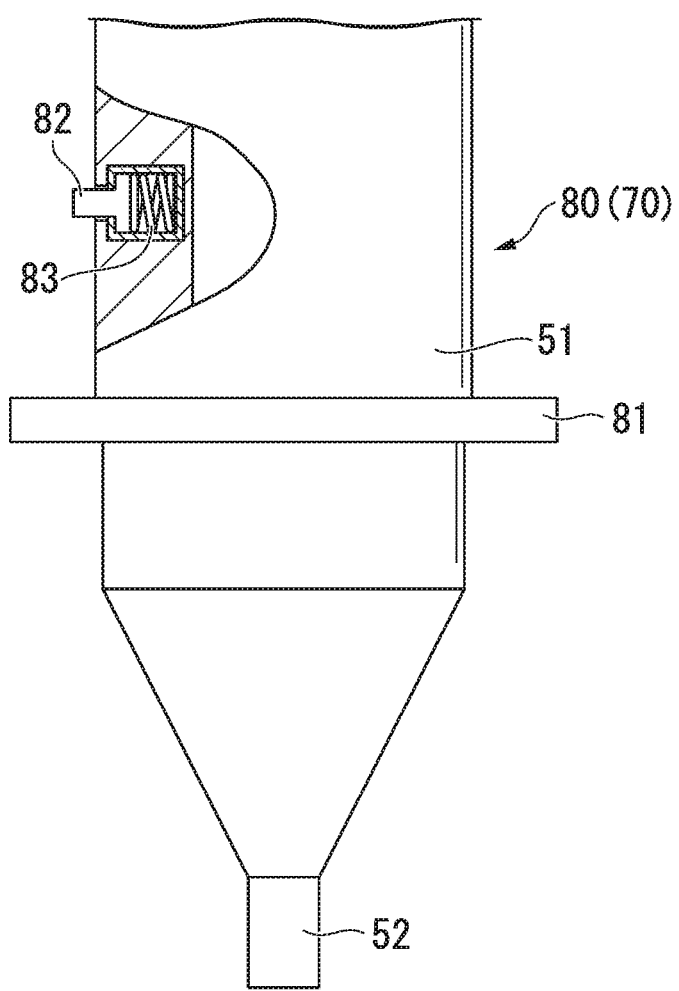
FIG. 10 is a view showing part of an inner needle portion of a medical instrument introduction device according to a second embodiment of the present invention.

FIG. 10 is a partially broken view showing a part of a distal end portion of the inner needle portion 80. The inner needle portion 80 has a flange 81 shown in FIG. 10, instead of the flange 53 shown in FIG. 4. The flange 81 is formed of a flexible material and formed in a disk shape. An outer diameter of the flange 81 is larger than an inner diameter of the distal end member 41 (see FIG. 11), however the flange 81 is deformable to enter inside of the distal end member 41. An engaging profection 82 is arranged on an outer circumference surface and more proximal than the flange 81 in the inner needle portion 80. The engaging projection 82 is biased to be projected from the outer circumference surface due to a spring 83, however the engaging projection 82 can be moved into inside the main body 51 by applying a force to a projection part of the engaging projection 82 to compress the spring 83.

Figure 11:
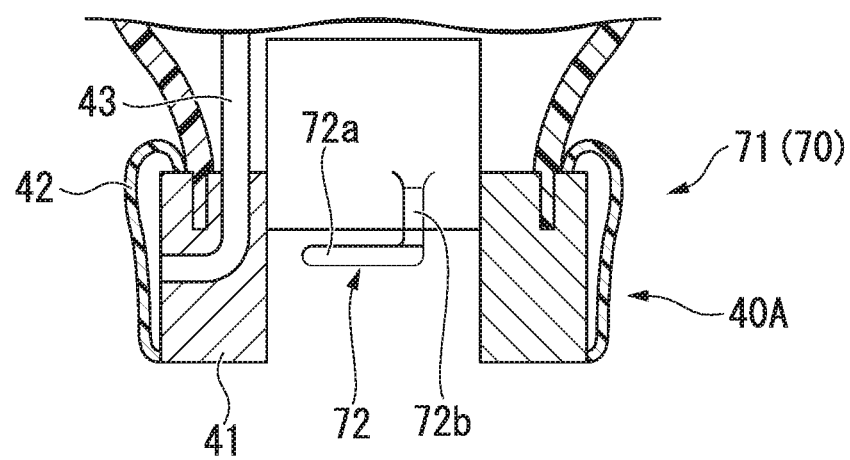
FIG. 11 is a partial cross-sectional view showing an outer tube portion of the medical instrument introduction device.

FIG. 11 is a cross-sectional view showing an anchor portion 40A of the outer tube portion 71. An engaged groove 72 is formed on an inner circumference surface of the distal end member 41, and a distal end portion of the engaging projection 82 can enter into the engaged groove 72. The engaged groove 72 has a first region 72a in parallel with a circumference direction of the distal end member 41, a second region 72b communicated with an end of the first region 72a. The second region 72b is extended in a direction in parallel with a longitudinal axis of the distal end member 41 and extended to a proximal end side of the distal end member 41. The depth of the engaged groove 72 in the first region 72a is a constant value, and a depth of the engaged groove 72 in the second region 72b gradually becomes smaller along a direction separating away from the first region 72a. The width of the second region 72b gradually becomes wider along the direction separating away from the first region 72a.

Figure 12:
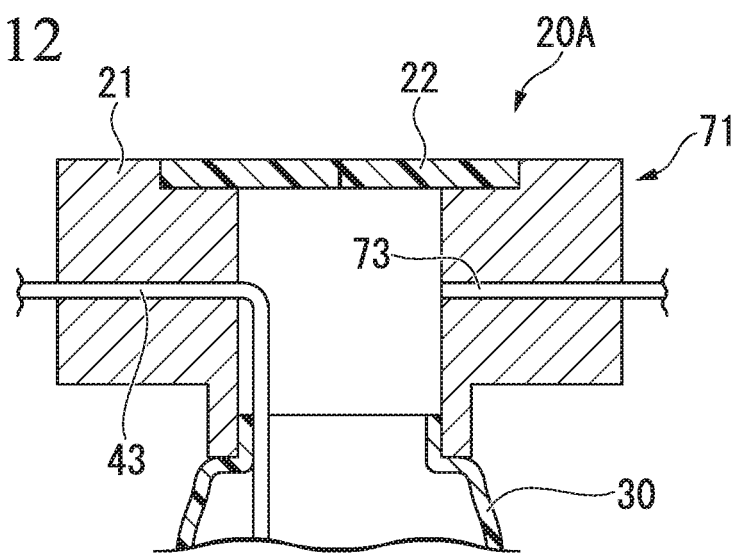
FIG. 12 is a partial cross-sectional view showing an outer tube portion of the medical instrument introduction device.

FIG. 12 is a cross-sectional view showing a base portion 20A of the outer tube portion 71. The base member 21 is attached with a second tube 73, besides the tube 43 attached for supplying the fluids to the balloon 42 (see FIG. 11). The second tube 73 is opened toward inside of the base member 21, and the second tube can be used for supplying fluids to inside of the conduit portion 30 and performing suction of the fluids inside of the conduit portion 30.

Operations of using the medical instrument introduction device 70 according to the present embodiment having the above-described outer tube portion 71 and the inner needle portion 80 will be described herewith.

When the user inserts the inner needle portion 80 into the outer tube portion 71, the engaging projection 82 is pressed by an inner circumference surface of the base member 21 to be accommodated inside the main body 51. After the flange 81 comes into contact with a proximal end surface of the distal end member 41, an edge of the flange 81 is deformed to be in a direction toward a side of the base portion 20A and the flange 81 enters inside of the distal end member 41. When the inner needle portion 80 furtherly moves with respect to the outer tube portion 71, the engaging projection 82 projects from the outer circumference surface of the inner needle portion 80 and enters the engaged groove 72 from the second region 72a. After the engaging projection 82 enters the first region 72a, the outer tube portion 71 and the inner needle portion 80 are engaged with each other. Since the width of the proximal end portion of the distal end member 41 is configured to be wide, it is easy to make the outer tube portion 71 and the inner needle portion 80 to be engaged with each other.

In a state in which the outer tube portion 71 and the inner needle portion 80 are engaged with each other, the anchor portion 40A follows advancement and retraction of the inner needle portion 80 to move integrally with the inner needle portion 80. That is, similar to the first embodiment, the anchor portion 40A can be separated away from the base portion 20A by advancing the inner needle portion 80. Further, the anchor portion 40A can easily approach the base portion 20A by retracting the inner needle portion 80.

That is, in the medical instrument introduction device 70, the conduit portion 30 can be easily to be stretched and compressed by advancing and retracting the inner needle portion 80 engaged with the outer tube portion 71 with respect to the outer tube portion 71, respectively.

Due to the deformation of the flange 81 inside the distal end member 41, a gap between the inner needle portion 80 and the distal end member 41 is filled. As a result, an inside of the outer tube portion 71 becomes a space where an airtight state is retained by the valve member 22 and the flange 81. In this state, when the suction is performed via the second tube 73, air inside the conduit portion 30 is removed. As a result, the conduit portion 30 deforms to closely contact with the inner needle portion 80, and the conduit portion 30 enters a state in which there is no sag formed with respect to the inner needle portion 80, the sag being generated since the conduit portion 30 is separated from the inner needle portion 80.

The engagement of the inner needle portion 80 and the outer tube portion 71 is released by rotating the inner needle portion 80 about a longitudinal axis thereof. Due to such an operation, the engaging projection 82 moves along the engaged groove 72 to a connection position of the first region 72a and the second region 72b. Subsequently, when the inner needle portion 80 is retracted, the engaging projection 82 moves in the second region 72b such that the engaging projection 82 is gradually pressed into the main body 51 and eventually the engaging projection 82 is out of the engaged groove 72.

According to the medical instrument introduction device 70 according to the present embodiment, as the same with the first embodiment, it is possible to change the length of the outer tube portion 71 in accordance with the distance between the indwelling position and the opening formation position such that the medical instrument can be suitably introduced into the luminal organs through the abdominal wall.

Since the outer tube portion 71 and the inner needle portion 80 can be engaged with each other, it is easy to adjust the length of the conduit portion 30.

Further, the second tube 73 is disposed such that the conduit portion 30 can be deformed to closely contact with the inner needle portion 80. As a result, even in a state in which the conduit portion is not completely stretched, the sag generated in the conduit portion can be suppressed to secure a state in which the distal end of the inner needle portion can be reliably observed.

In the present embodiment, in order to suitably perform the engagement of the engaging projection 82 and the engaged groove 72, an index (a marking) and the like, in accordance with a phase at which the engaged groove 72 is formed, may be provided at a proximal surface of the base portion 20A. At this time, the engagement can be more preferably performed once an index and the like is formed for indicating the position of the proximal end of the second region of the engaged groove 72.

Since the engagement mechanism of the outer tube portion and the inner needle portion, and the second tube have different functions, the medical instrument introduction device may be configured to have only one of them.

Preferred embodiments of the present invention have been described above, but the present invention is not limited to these embodiments or modifications thereof. Additions, omissions, replacements, and other changes of constituents can be made within a range not departing from the spirit of the present invention.

Firstly, in the medical instrument introduction device according to the present invention, the conduit portion is not specifically limited to the bellows folded shape. For example, the conduit portion may be configured to have an accordion shape formed by arranging a plurality of annular folding lines in the axial direction of the conduit portion, or the conduit portion may be folded to a bellows folded shape according to spiral folding lines.

When the folding lines are spiral-shaped, by arranging the tube spirally in accordance with the spiral folding lines or in parallel to the spiral folding lines, wherein the tube is used for supplying the fluids to the balloon of the anchor portion, there are advantages that interference against the stretch and compress of the conduit portion due to the tube can be suppressed, and the length adjustment of the tube can be unnecessary.

The balloon provided in the anchor portion is not essential. For example, instead of the balloon, an elastically deformable flange may be provided to realize a configuration that is engageable with the wall of the luminal organs.

Further, in the configuration of stretching the conduit portion by using the inner needle portion, instead of the above-mentioned abutment by the flange and the engagement between the projection and the groove, methods such as a frictional engagement due to force fitting and an engagement between a key and a keyway can be applied.

Additionally, the luminal organs as the treatment target of the medical instrument introduction device according to the present invention, is not limited to the above-mentioned large intestine. For example, the medical instrument introduction device according to the present invention is suitably applicable to the esophagus and the duodenum where the target site exists.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. A medical instrument introduction device, comprising:
  an outer tube portion that is configured to be indwelled within a body wall; and
  an inner needle portion that is configured to be inserted through the outer tube portion,
  wherein the outer tube portion includes:
    a base portion disposed at a proximal side of the outer tube portion;
    a tubular conduit portion, the conduit portion being formed of a stretchable material, a proximal end portion of the conduit portion being connected to the base portion; and
    an anchor portion connected to a distal end portion of the conduit portion,
  wherein:
  the conduit portion has a bellows folded shape in a natural state,
  a dimension of the conduit portion in an axial direction is capable of being increased as the folded shape is stretched by the inserted inner needle portion, and a force needed for stretching and increasing the dimension of the folded shape in the axial direction is gradually decreased in a direction from the proximal end portion toward the distal end portion of the conduit portion, such that the distal end portion of the folded shape stretches first when the inner needle portion is inserted into the conduit portion and exerts force on the folded shape, and
  the anchor portion and the inner needle portion are couplable with each other such that the anchor portion moves following an advancement or a retraction of the inner needle portion.

2. The medical instrument introduction device according to claim 1, wherein the anchor portion is deformable such that a maximum dimension of the anchor portion in a radial direction is larger than a dimension of the conduit portion in the radial direction.

3. The medical instrument introduction device according to claim 2, wherein the anchor portion includes a balloon which is expandable and shrinkable.

4. The medical instrument introduction device according to claim 1, wherein the inner needle portion includes a cauterization portion arranged at a distal end of the inner needle portion, the cauterization portion being configured to cauterize tissue by conducting electric current to the cauterization portion.

5. The medical instrument introduction device according to claim 1, wherein:
the inner needle portion includes an engaging projection projecting from an outer surface of the inner needle portion, and
the distal end portion includes a groove, and
the engaging projection is sized to fit into and slide along the groove so as to engage the outer tube portion and the inner needle portion.

6. A treatment method on a target site in a luminal organ inside a body cavity by using the medical instrument introduction device according to claim 1 and a flexible endoscope, the treatment method comprising:
a step of determining an indwelling position at which the outer tube portion of the medical instrument introduction device is to be indwelled within a body wall of the body cavity;
a step of forming a first opening communicating with the body cavity at the indwelling position;
a step of inserting the outer tube portion into the body cavity from a side of the anchor portion through the first opening, an insertion amount of the outer tube portion being determined such that at least the base portion is positioned outside the body cavity;
a step of inserting the endoscope through a natural opening and indicating an opening formation position at which a second opening communicating with the luminal organ inside the body cavity being formed, by using the endoscope, in order to confirm the opening formation position from outside of the luminal organ;
a step of inserting the inner needle portion into the outer tube portion until a distal end portion of the inner needle portion protrudes from the anchor portion and reaches a vicinity of the opening formation position, a bellows folded shape of the conduit portion being stretched;
a step of forming the second opening at the opening formation position by using the inner needle portion; and
a step of inserting the anchor portion into the luminal organ through the second opening, and deforming the anchor portion such that a dimension of the anchor portion in a radial direction becomes larger than that of the conduit portion to engage the anchor portion with the luminal organ.

7. The treatment method according to claim 6, further includes:
a step of removing the inner needle portion via the outer tube portion after the anchor portion is engaged with the wall of the luminal organ,
a step of inserting a medical instrument through the outer tube portion into the inside of the luminal organ,
a step of performing a treatment on the target site using the medical instrument together with another medical instrument introduced by the endoscope,
a step of removing the medical instrument through the outer tube portion after the treatment on the target site is finished, and
a step of shrinking the anchor portion and removing the outer tube portion from the luminal organ and the body cavity.

* * * * *